(12) United States Patent
Sorrentino et al.

(10) Patent No.: US 6,740,064 B1
(45) Date of Patent: May 25, 2004

(54) REUSABLE NONMETALLIC CANNULA

(75) Inventors: Greg Sorrentino, Wallingford, CT (US); Patrick Mozdzierz, Cromwell, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 0 days.

(21) Appl. No.: 09/566,555

(22) Filed: May 8, 2000

(51) Int. Cl.[7] .............................................. A61M 35/00
(52) U.S. Cl. ...................................................... 604/264
(58) Field of Search ............................ 604/274, 164.01

(56) References Cited

U.S. PATENT DOCUMENTS

| | | | |
|---|---|---|---|
| 3,986,508 A | * | 10/1976 | Barrington ............... 128/214.2 |
| 4,479,795 A | * | 10/1984 | Mustacich et al. ............ 604/53 |
| 4,762,688 A | | 8/1988 | Berry, Jr. |
| 4,870,125 A | * | 9/1989 | Nelson ....................... 524/490 |
| 4,999,415 A | | 3/1991 | Guiver et al. |
| 5,164,466 A | * | 11/1992 | El-Hibri et al. ............. 525/537 |
| 5,326,834 A | | 7/1994 | Sauers et al. |
| 5,333,620 A | * | 8/1994 | Moutafis et al. ............ 128/772 |
| 5,356,421 A | | 10/1994 | Castro |
| 5,520,664 A | * | 5/1996 | Bricault, Jr. et al. ........ 604/265 |
| 5,522,904 A | * | 6/1996 | Moran et al. ................. 623/22 |
| 5,549,565 A | | 8/1996 | Ryan et al. |
| 5,556,092 A | | 9/1996 | Theken |
| 5,603,702 A | | 2/1997 | Smith et al. |
| 5,633,331 A | | 5/1997 | Nichols et al. |
| 5,681,539 A | | 10/1997 | Riley |
| 5,722,829 A | | 3/1998 | Wilcox et al. |
| 5,743,436 A | | 4/1998 | Wilcox et al. |
| 5,755,362 A | | 5/1998 | Rodriguez, Jr. et al. |
| 5,756,145 A | * | 5/1998 | Darouiche ................. 427/2.24 |
| 5,769,863 A | | 6/1998 | Garrison |
| 5,871,471 A | * | 2/1999 | Ryan et al. ................. 604/167 |
| 5,883,150 A | | 3/1999 | Charkoudian |
| 5,893,858 A | | 4/1999 | Spitz |
| 6,036,711 A | | 3/2000 | Mozdzierz et al. |
| 6,099,544 A | * | 8/2000 | Wolf et al. ................. 606/185 |

FOREIGN PATENT DOCUMENTS

| | | |
|---|---|---|
| EP | 0450791 | 10/1991 |
| EP | 0454645 | 10/1991 |
| EP | 0781795 | 7/1997 |

OTHER PUBLICATIONS

B.L. Dickinson, XP–000984331, Udel/Radel, Polysulfone for Medical Applications.

* cited by examiner

*Primary Examiner*—Sharon Kennedy

(57) ABSTRACT

A reusable cannula that supports minimally invasive surgical procedures, such as endoscopic and thorascopic procedures, fabricated from a composition including polyarylsulfone material that is non-conductive, radiolucent, and sterilizable. The cannula is compatible with endoscopic devices as well as standard housing/seal and trocar systems.

12 Claims, 2 Drawing Sheets

FIG. 2
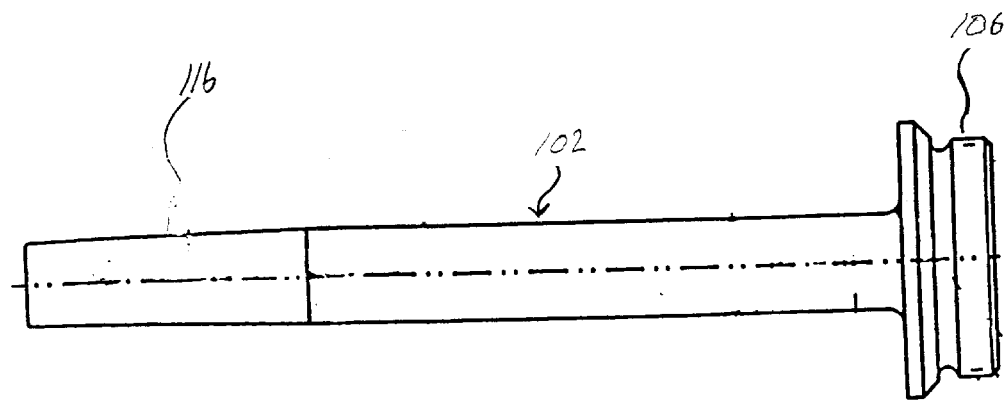
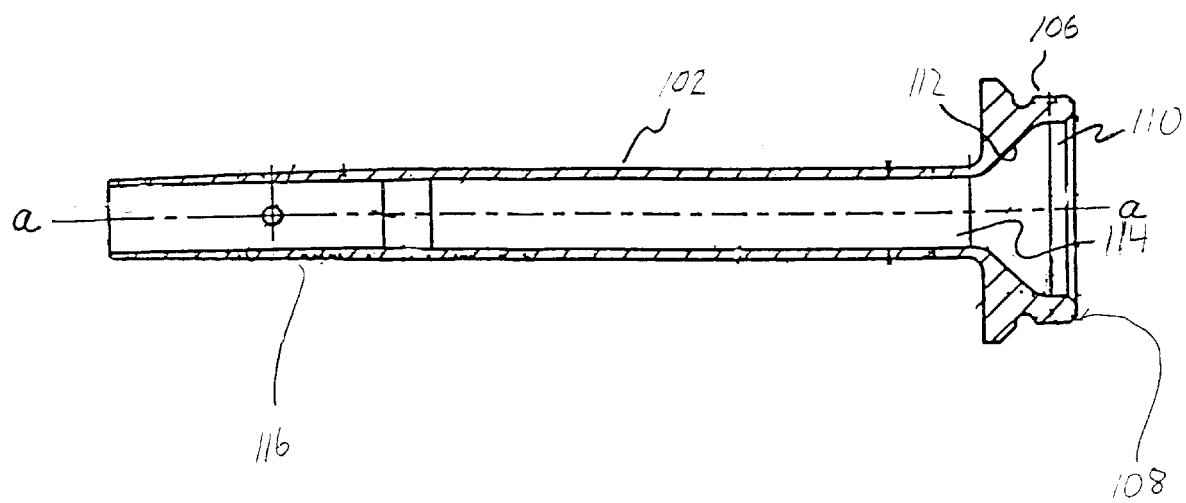
FIG. 3

REUSABLE NONMETALLIC CANNULA

BACKGROUND

1. Field of the Disclosure

The present disclosure relates to a reusable nonmetallic cannula for use in minimally invasive surgical procedures, and, in particular, to a cannula fabricated from a nonconductive radiolucent polyarylsulfone which is capable of withstanding repeated sterilizations.

2. Description of the Related Art

Cannulas are typically used in minimally invasive surgical procedures such as laparoscopic, endoscopic, and arthroscopic procedures. In minimally invasive procedures, the operating instrumentation is typically deployed through a narrow cannula inserted through a small opening or incision in the body to reach a remote interior operating site. In laparoscopic surgery, for example, the abdominal cavity is insufflated with a biologically non-reactive gas such as $CO_2$. A cannula assembly typically incorporating a cannula seal is introduced within the body cavity, and laparoscopic surgical instrumentation is advanced within the cannula to perform the surgical procedure. The seal within the cannula assembly forms a fluid-tight seal about the instrumentation to prevent egress of gas from the cavity.

From a cost efficiency point of view, it may be desirable to utilize cannula assemblies which can be reused, in whole, or in part. However, reuse of a cannula assembly requires disassembly, cleaning and sterilization of its component. Sterilization is typically accomplished through an autoclaving process which involves subjecting the cannula with superheated sterilizing steam under pressure. In the past, cannulas which have been typically fabricated from metals such as stainless steel are capable of withstanding a minimum number of autoclaving processes. However, disadvantages associated with the use of metallic cannulas are their electrically conductive properties, radiopaque qualities, and their relatively high expense of manufacture.

Accordingly, it is desirable to provide a cannula which is reusable, electrically non-conductive, radiolucent, easily assembled and disassembled for autoclaving, capable of withstanding repeated sterilizations, and relatively inexpensive to manufacture.

SUMMARY

In accordance with the present disclosure, a reusable nonmetallic cannula for use in minimally invasive surgical procedures, such as endoscopic and laparoscopic procedures, is disclosed. The cannula is preferably fabricated from a polyarylsulfone that is non-conductive, radiolucent, and capable of being subjected to repeated sterilizations. The cannula is configured to be compatible with a wide range of standard housing/seal and trocar systems and can be produced in a wide range of individual sizes and lengths.

BRIEF DESCRIPTION OF THE DRAWINGS

Preferred embodiments of the disclosure are described herein with reference to the drawings, wherein:

FIG. 2 is a side plan view of the cannula sleeve of the cannula assembly of FIG. 1; and FIG. 3 is a cross-sectional view of the cannula sleeve.

DETAILED DESCRIPTION OF THE PREFERRED EMBODIMENTS

Figure 1:
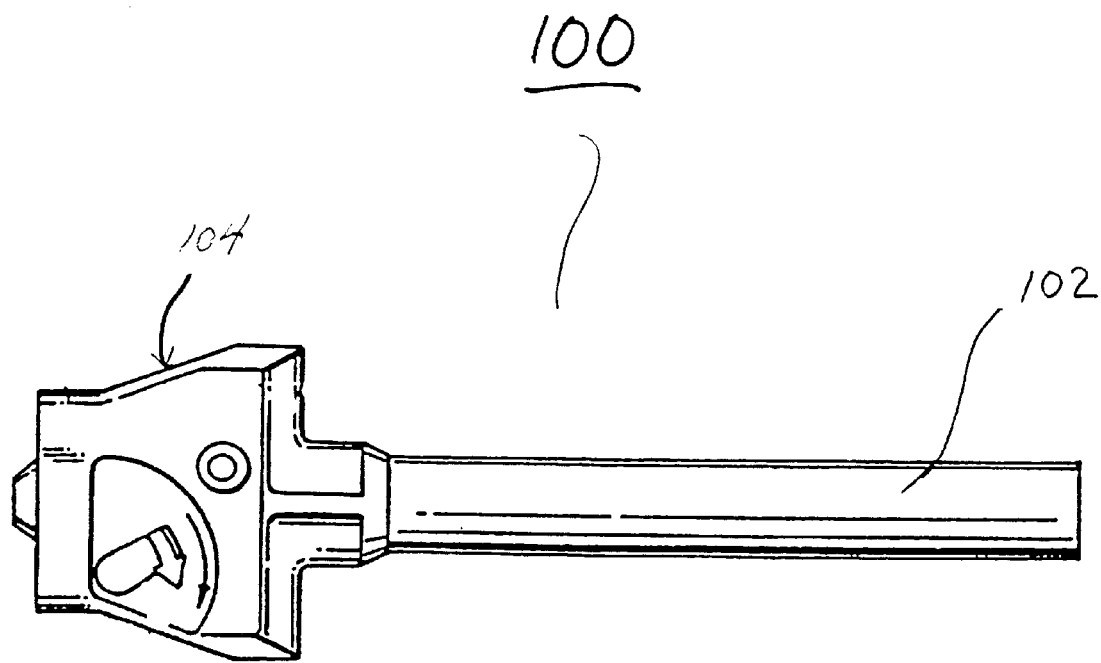
FIG. 1 is a side plan view of the cannula assembly in accordance with the principles of the present disclosure, including the cannula housing and the cannula sleeve.

In the discussion which follows, the term "proximal" as is traditional will refer to the portion of the structure which is closest to the operator and the term "distal" will refer to the portion which is furthest from the operator.

The cannula assembly of the present disclosure is particularly intended for use with a trocar assembly in performing laparoscopic surgical procedures. However, it is appreciated that the present disclosure is not intended to be limited to such use, but may be incorporated in a variety of surgical cannula or catheter assemblies including, for example, introvascular cannulas or catheters such as aortic or venous cannulas, etc.

Referring to the drawings in detail, and initially to FIG. 1, the presently disclosed reusable nonmetallic cannula assembly 100 includes cannula sleeve 102 and cannula housing 104 attached to the cannula sleeve 102. Cannula sleeve 102 is fabricated from a composition which includes a polyarylsulfone. Polyarylsulfones are generally clear, rigid thermoplastics possessing glass transition temperatures of about 180° to about 250° C., tensile strengths of at least about 10,000 psi, and flexural strengths of at least about 15,000 psi. Polyarylsulfones display minimum creep and low expansion coefficients and remain in their configured and machined shape over a wide range of temperatures as well as time. Polyarylsulfones, while soluble in certain aromatic hydrocarbons, are resistant to corrosive acid and alkalies as well as to heat, oxidation, detergents, oils and alcohols. Polyarylsulfones are dimensionally stable over temperatures ranging from –100 to +148° C. They can be readily processed and fabricated, and have been employed in the fabrication of power tool housings, electrical equipment, automobile components, electronic parts and computer components. The use of polyarylsulfones in accordance with the present invention is believed to be not only a novel use for these materials, but a use which is ideally suited due to the properties of polyarylsulfones. These particular properties allow the material to be of suitable strength and durability for the intended purpose disclosed herein. Further general information about polyarylsulfones can be obtained by reference to the Encyclopedia of Polymer Science and Engineering, Vol. 13, pp. 198–211, John Wiley & Sons, Second Edition (1988), the contents of which are incorporated herein by reference. Polyarylsulfones utilized in accordance with the practice of the present disclosure can be generally described as containing backbone aromatic rings which are linked, preferably paralinked, partly by sulfone groups (—$SO_2$—) and partly by dissimilar groups such as ether or alkyl groups or single bonds. In general, the repeating units of polyarylsulfones can be represented as follows:

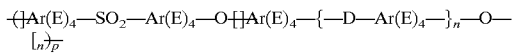

where Ar is a 6 to 20 carbon aromatic radical, preferably phenylene; D is (a) a divalent hydrocarbyl radical, of which all or different portions can be (i) linear, branched, cyclic or bicyclic, (ii) aliphatic or aromatic, and/or (iii) saturated or unsaturated, said divalent hydrocarbyl radical being composed of 1–35 carbon atoms together with up to five oxygen, nitrogen, sulfur and/or halogen (such as fluorine, chlorine and/or bromine) atoms; or (b) a divalent S, $S_2$, SO, $SO_2$, O or CO radical; or (c) a single bond; each E is independently hydrogen, a halogen (such as fluorine, chlorine and/or bromine), a $C_1$–$C_{12}$, preferably $C_1$–$C_8$, linear or cyclic alkyl, aryl, alkaryl, aralkyl, alkoxy or aryloxy radical, such as methyl, ethyl, isopropyl, cyclopentyl, cyclohexyl, methoxy, ethoxy, benzyl, tolyl, xylyl, phenoxy and/or xylynoxy; or a nitro or nitrile radical; m is 0 or 1; and n is from 0 to about 3, and p is from about 1 to about 500. Preferably D is a single bond or a divalent hydrocarbyl radical, preferably composed of 1–10 carbon atoms, and is preferably isopropylidene. Preferably each E is independently hydrogen, a halogen, a $C_1$–$C_8$ alkyl, alkaryl, aralkyl, or aryl radical.

In preferred polyarylsulfones according to the formula above,

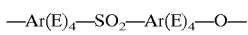

represents a remnant of a 4,4"-dihalodiphenyl sulfone (e.g., dichlorodiphenylsulfone) or a sulfone-bridged bisphenol (e.g., bisphenol S) and

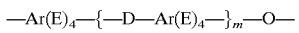

represents a remnant of an optional dihydric compound, preferably Bisphenol-A.

Preferred polyarylsulfones are commonly prepared from a 4,4'-dihalodiphenyl sulfone and a second, optional dihydric compound, such as Bisphenol-A, in a dipolar aprotic solvent such as dimethyl sulfoxide or 1-methyl-2-pyrrolidinone. A fluoride or chloride may be used as the dihalodiphenyl sulfone monomer. Another variety of polyarylsulfone is synthesized from a bisphenol which contains a sulfone bridge ("Bisphenol-S").

Other bisphenols, in addition to Bisphenol-A, which can be utilized to prepare polyarylsulfones include, but are not limited to, 4,4'-dihydroxydiphenyl sulfide, 4,4'-dihydroxydiphenyl oxide, 4,4'-dihydroxydiphenylmethane, hydroquinone, bis(4-hydroxydiphenyl)-2,2-perfluoropropane, bis(4-hydroxydiphenyl)-1,1-cyclohexane, 4,4'dihydroxybenzophenone, and 4,4'-dihydroxydiphenyl.

The polyarylsulfones suitable for use in accordance with the present disclosure desirably possess molecular weights (weight average) of at least about 10,000, preferably at least about 25,000, and more preferably at least about 35,000, and most preferably up to about 200,000. Suitable melt flow rates as measured in grams per 10 minutes by ASTM D1238, (343° C., 8.7 kg) range from at least about 1, preferably at least about 2, more preferably at least about 3 up to about 30, preferably up to about 20 and more preferably up to about 10.

Some examples of the suitable types of polyarylsulfones that are commercially available are Victrex™ polyether polyarylsulfones from ICI Americas, Inc.; Udel™ bisphenol-A polyarylsulfones from Amoco Performance Products, Inc.; Radel A™ polyarylethersulfones from Amoco Performance Products, Inc.; and Radel R™ polyphenylsulfones from Amoco Performance Products, Inc. In accordance with a preferred embodiment, the polyarylsulfone is a polyphenylsulfone, such as Radel R™ polyphenylsulfones from Amoco Performance Products, Inc. Blends of two or more polyarylsulfones can also be employed.

It is within the scope of the present disclosure to employ blends of polyarylsulfones with one or more polymeric materials not containing the above described repeating units in order to enhance the functional properties of reusable cannula 100. Thus, e.g., to improve chemical resistance, flow properties, impact resistance, and the like, polyarylsulfone can be blended with, for example, polyesters, styrene polymers, elastomers, and the like. The amount of such optionally added polymeric materials will usually represent up to about 25 weight percent of the entire blend composition, preferably from about 5 to about 25, more preferably from about 10 to about 20 weight percent. A variety of additives may be advantageously admixed with polyarylsulfones singly or in combination, such as, e.g., antimicrobial agents, antioxidants, opacifying agents, antistatic agents, fillers, reinforcing agents, hydrolytic stabilizers, stabilizers against basic impurities, lubricants, mold release agents, pigments, dyes, opacifying agents, colorants, plasticizers, heat stabilizers, and ultraviolet light stabilizers. Preferred hindered phenolic antioxidants are Irganox™ 1076 and Irganox™ 1010 antioxidants, available from Ciba-Geigy Corp. Such additives, if used will typically represent from about 0.001 to about 15 percent, preferably from about 0.01 to about 10 percent and more preferably from about 0.1 to about 10 percent by weight of the total composition.

Polyarylsulfones are non-conductive, radiolucent, resistant to degradation by combinations of moisture and temperature, and provide at the least the same or reduced instrument friction as existing instruments. The radiolucent characteristic is desirable in certain surgical applications involving the cannula sleeve 102, e.g., to permit radiation of tissue underlying the sleeve 102 without the removal therefrom. When softened or melted by the application of heat, they are formed, shaped or molded and then machined into the cannula of the present disclosure, using conventional techniques such as compression molding, injection molding, gas assisted injection molding, calendering, vacuum forming, themoforming, extrustion and/or blow molding techniques, alone or in combination.

Polyarylsulfones possess the desirable characteristic of being sufficiently durable to withstand repeated microwave cycles. Cannula sleeve 102 is thus capable of withstanding repeated sterilizations using standard methods such as, but not limited to, microwave and steam autoclave. While polyarylsulfones are typically transparent, the polyarylsulfones utilized in accordance with the present disclosure preferably are opacified with an opacifying agent.

Cannula housing 104 is adapted to sealingly lock with cannula sleeve 102. The sizes of cannula sleeve 102 include, but are not limited to 5, 10, 11, and 12 millimeters. While a shortened length for the 5 mm and an increased length for the 10 mm sizes are envisioned to enhance selected procedures, these as well as other variations in length are readily adapted for any size.

Referring now to FIGS. 2–3, the structural details of cannula sleeve 102 will be discussed. At its proximal end, cannula sleeve 102 contains a flange 106 with an attachment mechanism 108 that sealingly mates with cannula housing 104. The inside circumference of flange 106 defines a circular opening 110 that makes a transition 112 to a reduced-diameter longitudinal circular throughhole 114. Cannula sleeve 102 defines longitudinal axis "a" and is generally cylindrically-shaped as shown. The wall of cannula sleeve 102 has a generally uniform thickness.

Cannula housing 104 may be readily mounted to the proximal end of cannula sleeve 102. Cannula housing 104 typically incorporates a seal which provides a substantial seal between a body cavity of a patient and the outside atmosphere both during insertion and removal of an instrument through the cannula. In this manner, insufflation gases are prevented from escaping through the trocar assembly to the outside environment. One seal mechanism contemplated is the mechanism disclosed in commonly assigned U.S. Pat.

No. 5,603,702 entitled, "Valve System for Cannula Assembly", which issued Feb. 18, 1997 the contents of which are hereby incorporated by reference. Other housing sealing, and locking configurations are also envisioned for cannula 100.

The attachment mechanism 108 of cannula sleeve 102 preferably includes threads that sealingly engage corresponding internal threads (not shown) of housing 104, however, other attachment mechanisms, including bayonet locking mechanisms, snap fit structure, adhesives are also contemplated. The preferred threaded configuration of the present invention thus provides an easy means for assembly, sealing, and subsequent sterilization. The distal end of cannula sleeve 102 includes a tapered portion 116 that reduces the thickness of the wall of sleeve 102 and an air hole approximately 0.5 inches from the distal end.

Cannula 100 is configured to be used in various tissue layers encountered during endoscopic procedures, to include both in vivo in humans and animals as well as in vitro applications.

The following example illustrates the practice of the present invention:

EXAMPLE

A polyarylsulfone commercially sold under the tradename Radel™, R-5000 by Amoco Performance Products, Inc. was injection molded and machined to form cannulas in the configuration of the present disclosure, such as 5, 10, 11, and 12 mm diameters and standard lengths. The cannulas under test were production representative and possessed sufficient strength to support penetrating tissue layers, act as a conduit for a trocar, support minimally invasive surgery, and provide a seal with other instrumentation to prevent the passage of undesirable fluids into or out of the invasive surgery after repeated sterilization cycles. The cannulas were subjected to over 100 autoclave sterilization test cycles which approximates the number of times a reusable cannula is sterilized during a typical year's usage. The experimental results after 100 autoclave cycles showed no degradation to the mechanical strength of the cannulas or their ability to provide an adequate seal when attached to the Versaport™ disposable housing/seal system, or its equivalent, and thus validated the ability of this configuration to support surgical procedures after a typical year's usage.

Although the illustrative embodiments of the present disclosure have been described herein with reference to the accompanying drawings, it is to be understood that the disclosure is not limited to those precise embodiments, and that various other changes and modifications may be affected therein by one skilled in the art without departing from the scope or spirit of the disclosure. All such changes and modifications are intended to be included within the scope of the disclosure.

What is claimed is:

1. A reusable nonmetallic cannula assembly comprising a cannula sleeve fabricated from a composition which includes a nonconductive, sterilizable polyarylsulfone.

2. The cannula assembly according to claim 1, wherein the polyarylsulfone comprises repeating units of the formula:

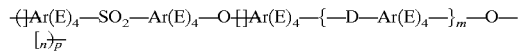

where Ar is a 6 to 20 carbon aromatic radical; D is (a) a divalent hydrocarbyl radical, of which all or different portions can be (i) linear, branched, cyclic or bicyclic, (ii) aliphatic or aromatic, and/or (iii) saturated or unsaturated, said divalent hydrocarbyl radical being composed of 1–35 carbon atoms together with up to five oxygen, nitrogen, sulfur and/or halogen atoms; or (b) a divalent S, $S_2$, SO, $SO_2$, O or CO radical; or (c) a single bond; each E is independently hydrogen, a halogen, a $C_1$–$C_{12}$ hydrocarbyl radical or a nitro or nitrile radical; m is 0 or 1; and n is from 0 to about 3, and p is from 1 to about 500.

3. The cannula assembly according to claim 2, wherein Ar is phenylene, D is a single bond or a divalent hydrocarbyl radical and each E is independently hydrogen, halogen or $C_1$–$C_{12}$ hydrocarbyl radical.

4. The cannula assembly according to claim 1, wherein the composition further comprises one or more polymeric materials.

5. The cannula assembly according to claim 4, wherein the polymeric materials are selected from the group consisting of polyesters, styrene polymers and elastomers.

6. The cannula assembly according to claim 1, wherein the composition further comprises one or more additives selected from the group consisting of antimicrobial agents, antioxidants, opacifying agents, antistatic agents, fillers, reinforcing agents, hydrolytic stabilizers, stabilizers against basic impurities, lubricants, mold release agents, pigments, dyes, colorants, plasticizers, heat stabilizers, and ultraviolet light stabilizers.

7. A cannula assembly according to claim 1, wherein the cannula can withstand in excess of 100 sterilization cycles without substantially degrading its structural integrity.

8. The cannula assembly according to claim 1, further including a cannula housing mounted to the cannula.

9. The cannula according to claim 1, wherein the cannula contains a proximal end comprising an attachment mechanism and a sheath connected to the proximal end.

10. The cannula according to claim 9, wherein the proximal end comprises a monolithically formed housing.

11. A reusable nonmetallic cannula assembly comprising a cannula sleeve fabricated from a composition which includes a nonconductive, sterilizable polyarylsulfone and one or more additives admixed with the polyarylsulfone singly or in combination selected from the group consisting of antimicrobial agents and mold release agents.

12. A reusable nonmetallic cannula assembly comprising a cannula sleeve fabricated from a composition which includes a nonconductive, sterilizable polyarylsulfone and one or more additives admixed with the polyarylsulfone singly or in combination selected from the group consisting of antioxidants and ultraviolet light stabilizers.

* * * * *